US011035857B2

(12) United States Patent
Reubinoff et al.

(10) Patent No.: US 11,035,857 B2
(45) Date of Patent: *Jun. 15, 2021

(54) METHODS OF SELECTING RETINAL PIGMENTED EPITHELIAL CELLS

(71) Applicants: Cell Cure Neurosciences Ltd., Jerusalem (IL); Hadasit Medical Research Services and Development Ltd., Jerusalem (IL)

(72) Inventors: Benjamin Eithan Reubinoff, Moshav Bar-Giora (IL); Nurit Yachimovich-Cohen, Jerusalem (IL); Limor Matzrafi, Reut (IL)

(73) Assignees: Hadasit Medical Research Services and Development Ltd., Jerusalem (IL); Cell Cure Neurosciences Ltd., Jerusalem (IL)

(*) Notice: Subject to any disclaimer, the term of this patent is extended or adjusted under 35 U.S.C. 154(b) by 0 days.

This patent is subject to a terminal disclaimer.

(21) Appl. No.: 15/470,926

(22) Filed: Mar. 28, 2017

(65) Prior Publication Data

US 2017/0199190 A1    Jul. 13, 2017

Related U.S. Application Data

(62) Division of application No. 14/375,195, filed as application No. PCT/IL2013/050077 on Jan. 29, 2013, now Pat. No. 9,658,216.

(60) Provisional application No. 61/592,635, filed on Jan. 13, 2012.

(51) Int. Cl.
| G01N 33/569 | (2006.01) |
| C12N 5/079 | (2010.01) |
| G01N 33/52 | (2006.01) |
| G01N 33/58 | (2006.01) |
| G01N 21/64 | (2006.01) |
| G01N 21/47 | (2006.01) |

(52) U.S. Cl.
CPC ..... G01N 33/56966 (2013.01); C12N 5/0621 (2013.01); G01N 33/52 (2013.01); G01N 33/582 (2013.01); C12N 2501/15 (2013.01); C12N 2501/16 (2013.01); C12N 2506/45 (2013.01); C12N 2509/00 (2013.01); G01N 21/6486 (2013.01); G01N 2021/4704 (2013.01); G01N 2333/46 (2013.01)

(58) Field of Classification Search
CPC ............ G01N 33/52; G01N 21/6486; G01N 2021/4704; C12N 5/0621; C01N 2333/46
See application file for complete search history.

(56) References Cited

U.S. PATENT DOCUMENTS

| 9,658,216 B2* | 5/2017 | Reubinoff ............. G01N 33/52 |
| 2010/0105137 A1 | 4/2010 | Takahashi et al. |
| 2011/0027333 A1 | 2/2011 | Idelson et al. |
| 2015/0010922 A1 | 1/2015 | Reubinoff et al. |

FOREIGN PATENT DOCUMENTS

| WO | WO 2008/129554 | 10/2008 |
| WO | WO 2013/114360 | 8/2013 |

OTHER PUBLICATIONS

Maecker et al., Cytometry Part A, 69A: 1037-1042, 2006.*
Yuan, "Forward & Side Scatter Optimization Protocol", obtained from https://www.sickkids.ca/research/FCF/documents/tools/FSCSSCvoltoptProtocolver2.pdf, 2010; accessed on Jul. 8, 2017, pp. 1-2.*
International Preliminary Report on Patentability dated Aug. 14, 2014 From the International Bureau of WIPO Re. Application No. PCT/IL2013/050077.
International Search Report and the Written Opinion dated May 20, 2013 From the International Searching Authority Re. Application No. PCT/IL2013/050077.
Notice of Allowance dated Dec. 23, 2016 From the US Patent and Trademark Office Re. U.S. Appl. No. 14/375,195. (9 pages).
Official Action dated Oct. 8, 2015 From the US Patent and Trademark Office Re. U.S. Appl. No. 14/375,195.
Official Action dated Jul. 25, 2016 From the US Patent and Trademark Office Re. U.S. Appl. No. 14/375,195.
BD Biosciences "BD FACSCanto II Flow Cytometer. Technical Specifications", BD Biosciences, Retrieved From the Internet, 4 P., Mar. 28, 2011. p. 1, 2.
Ben-Shabat et al. "Fluorescent Pigments of the Retinal Pigment Epithelium and Age-Related Macular Degeneration", Bioorganic & Medicinal Chemistry Letters, 11(12): 1533-1540, Jun. 18, 2001.
Burke et al. "Autofluorescent Inclusions in Long-Term Postconfluent Cultures of Retinal Pigment Epithelium", Investigative Ophthalmology & Visual Science, 39(8): 1478-1486, Jul. 1998. p. 1479, col. 2, Para 2, p. 1481, Fig.1.
Kellner et al. "Lipofuscin- and Melanin-Related Fundus Autofluorescence Visualize Different Retinal Pigment Epithelial Alterations in Patients With Retinitis Pigmentosa", Eye, 23(6): 1349-1359, Published Online Sep. 12, 2008.

(Continued)

Primary Examiner — Thaian N. Ton
(74) Attorney, Agent, or Firm — Mintz, Levin, Cohen, Ferris, Glovsky and Popeo, P.C.

(57) ABSTRACT

A method of selecting retinal pigmented epithelial (RPE) cells from a mixed population of cells is disclosed. The method comprises:
(a) analyzing the cells of the mixed population of cells for at least one of the following parameters:
  (i) cells which autofluorescence above a predetermined threshold;
  (ii) cells which express CD81 above a predetermined threshold; and
  (iii) cells which scatter light perpendicular to a laser beam above a predetermined threshold; and
(b) selecting cells which are positive for at least one of the parameters, thereby sorting RPE cells from a mixed population of cells.

30 Claims, 8 Drawing Sheets
(6 of 8 Drawing Sheet(s) Filed in Color)

(56) References Cited

OTHER PUBLICATIONS

Klimanskaya "Retinal Pigment Epithelium", Methods in Enzymology, 418(Art.11): 169-194, 2006.
Lako "Identification of Cell Surface Markers for Human Stem Cell Derived Photoreceptors Using the BD Lyoplate™ Screening Panel", BD Bioscience Research Grant Program Winning Abstract, 2011.
Nighswander-Rempel et al. "Melanin Autofluorescence in Cancerous and Normal Melanocytes", Retrieved From the Internet Focusmicroscopy.org, Presentation Abstract, 2006.
Pan et al. "The Developmental Regulation of CD81 in the Rat Retina", Molecular Vision, 13: 181-189, 2007. p. 183, Fig.3, p. 185, col. 1, Para 1, col.2, Para 2, p. 186, col. 1, Para 1.
Rowland et al. "Pluripotent Human Stem Cells for the Treatment of Retinal Disease", Journal of Cellular Physiology, 227: 457-466, 2012.
Wassell et al. "Fluorescence Properties of Autofluorescent Granules Generated by Cultured Human RPE Cells", Investigative Ophthalmology & Visual Science, 39(8): 1487-1492, Jul. 1998.
Zucker et al. "Detection of Ti02 Nanoparticles in Cells by Flow Cytometry", Cytornety Part A 77(7): 677-685, Jul. 1, 2010.
Examination Report dated Sep. 1, 2017 From the Australian Government, IP Australia Re. Application No. 2013216382. (3 Pages).
Surre et al. (Aug. 14, 2018), "Strong Increase in the Autofluorescence of Cells Signals Struggle for Survival", Scientific Reports, 8(1):12088:14 pages.

\* cited by examiner

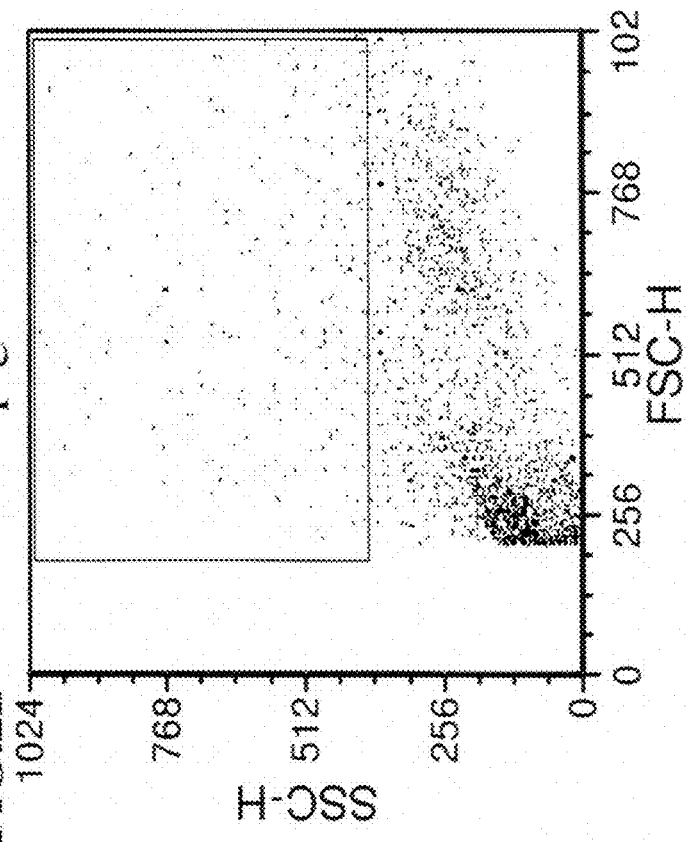
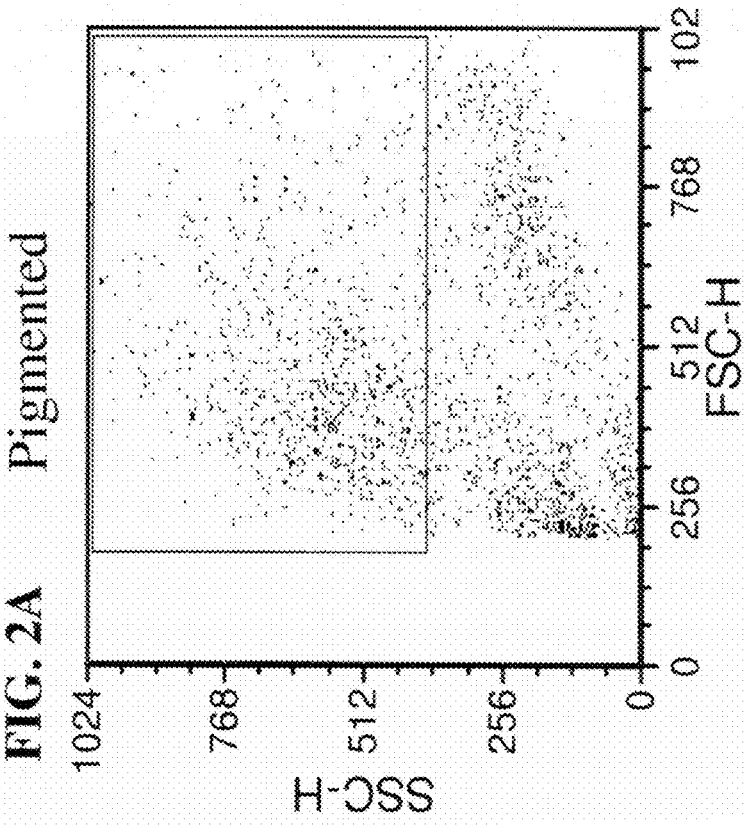

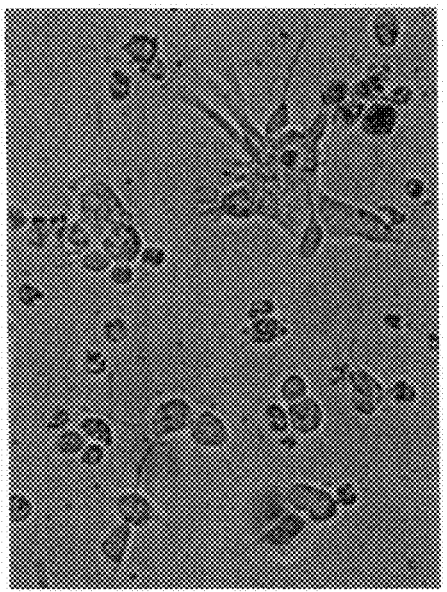
FIG. 5A — Autofluorescent
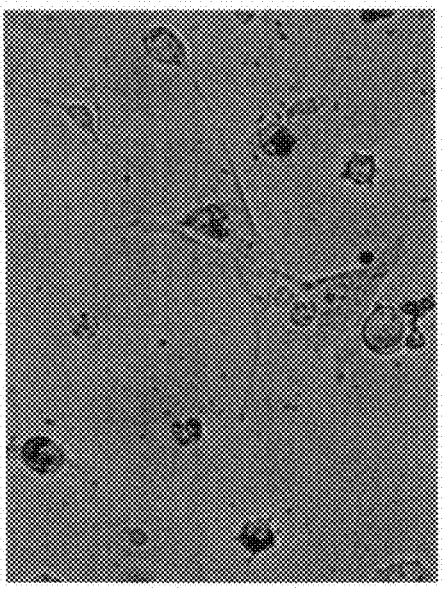
FIG. 5B — High SSC
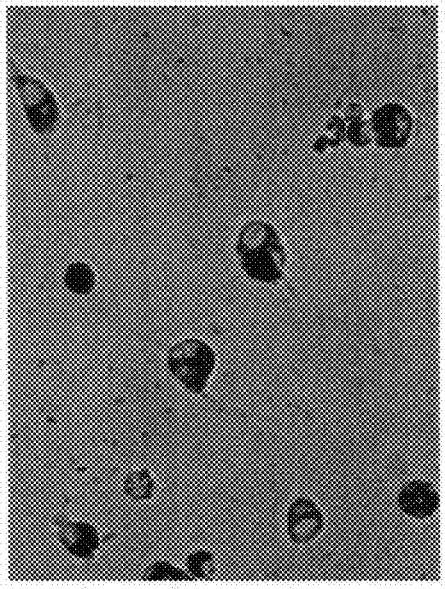
FIG. 5C — Low SSC

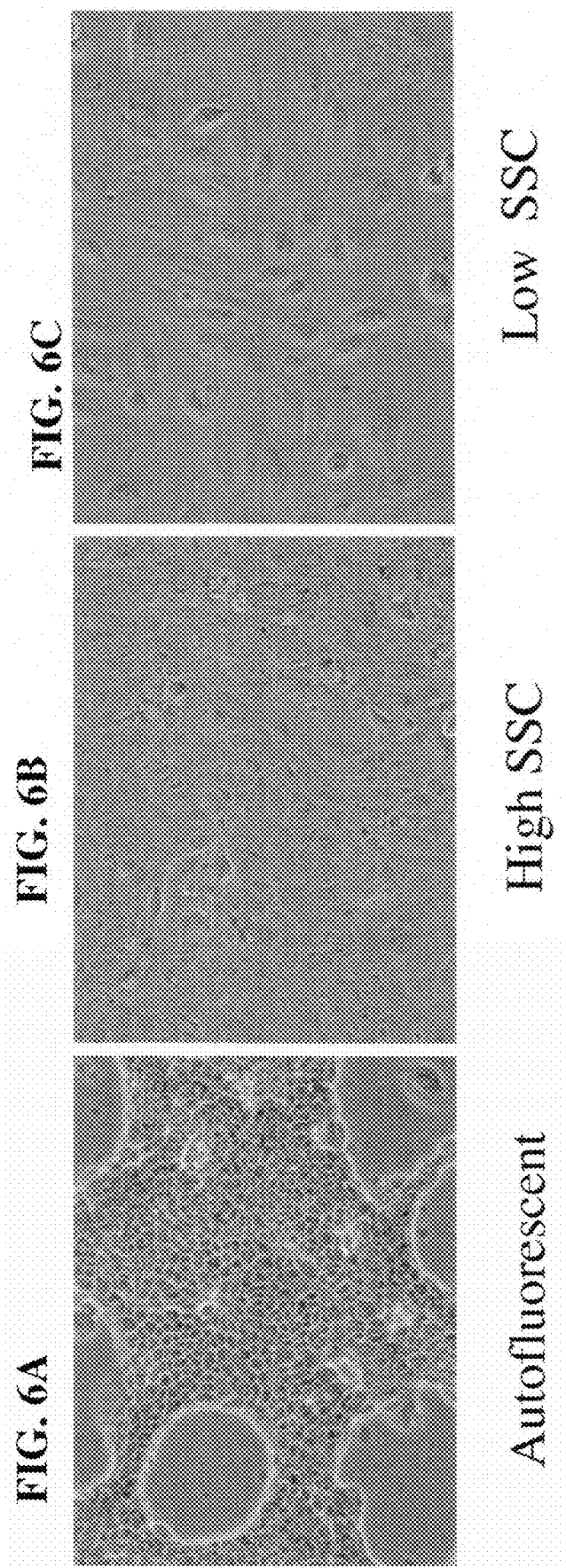
FIG. 6A Autofluorescent
FIG. 6B High SSC
FIG. 6C Low SSC

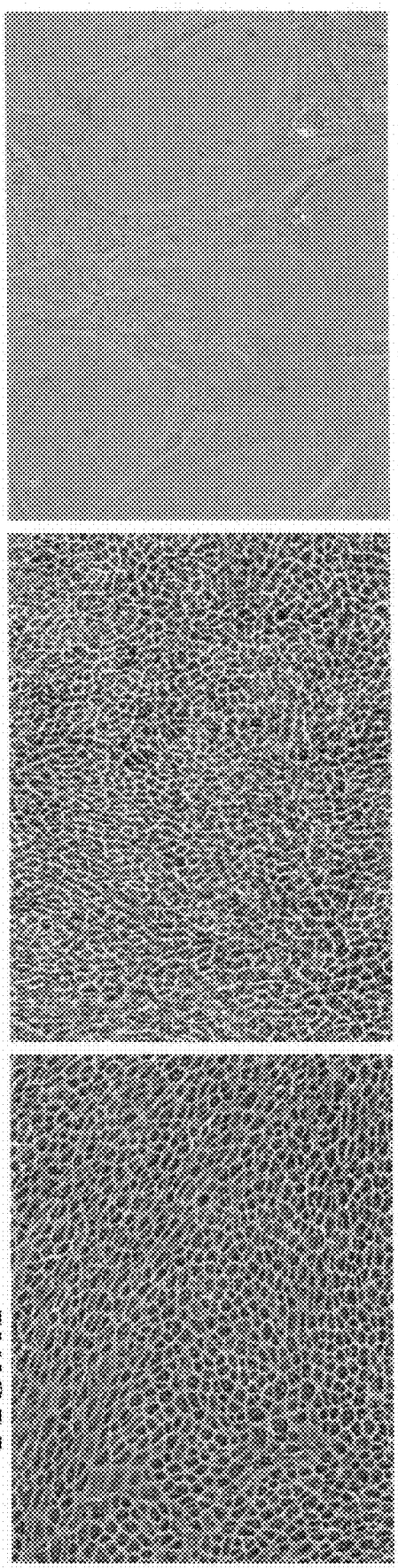
FIG. 7A  Autofluorescent
FIG. 7B  High SSC
FIG. 7C  Low SSC

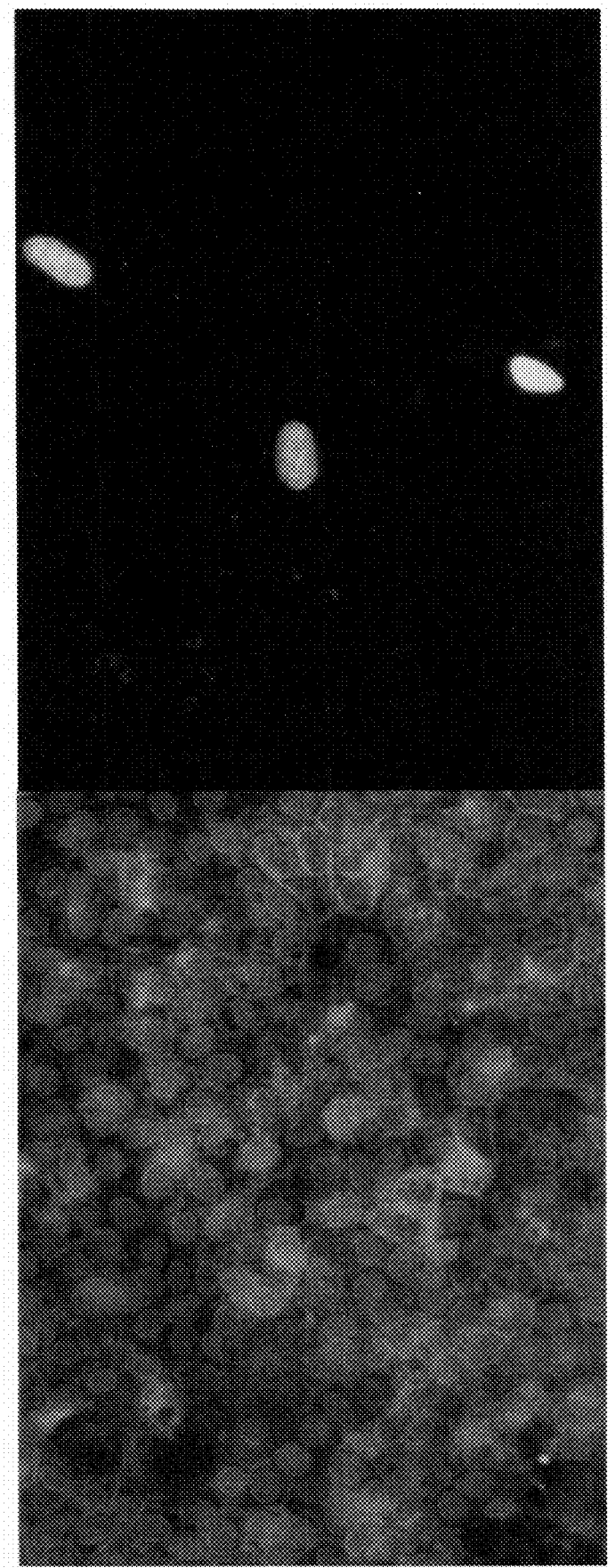

METHODS OF SELECTING RETINAL PIGMENTED EPITHELIAL CELLS

RELATED APPLICATIONS

This application is a divisional of U.S. patent application Ser. No. 14/375,195 filed on Jul. 29, 2014, which is a National Phase of PCT Patent Application No. PCT/IL2013/050077 having International Filing Date of Jan. 29, 2013, which claims the benefit of priority of U.S. Provisional Patent Application No. 61/592,635 filed on Jan. 31, 2012.

The contents of the above applications are all incorporated by reference as if fully set forth herein in their entirety.

FIELD AND BACKGROUND OF THE INVENTION

The present invention, in some embodiments thereof, relates to methods of selecting retinal pigmented epithelial cells (RPE cells).

The retinal pigmented epithelium (RPE) is a monolayer of pigmented cells, which lies between the neural retina and the choriocapillars. The RPE cells play crucial roles in the maintenance and function of the retina and its photoreceptors. These include the formation of the blood-retinal barrier, absorption of stray light, supply of nutrients to the neural retina, regeneration of visual pigment, and uptake and recycling of shed outer segments of photoreceptors.

Retinal tissue may degenerate for a number of reasons. Among them are: artery or vein occlusion, diabetic retinopathy and retinopathy of prematurity, which are usually hereditary. Diseases such as retinitis pigmentosa, retinoschisis, lattic degeneration, Best disease, and age related macular degeneration (AMD) are characterized by progressive types of retinal degeneration.

RPE cells may potentially be used for cell replacement therapy of the degenerating RPE in retinal diseases mentioned above. It may be also used as a vehicle for the introduction of genes for the treatment of retinal degeneration diseases. These cells may also serve as an in vitro model of retinal degeneration diseases, as a tool for high throughput screening for a therapeutic effect of small molecules, and for the discovery and testing of new drugs for retinal degeneration diseases. RPE cells could also be used for basic research of RPE development, maturation, characteristics, properties, metabolism, immunogenicity, function and interaction with other cell types.

Human fetal and adult RPE has been used as an alternative donor source for allogeneic transplantation. However, practical problems in obtaining sufficient tissue supply and the ethical concerns regarding the use of tissues from aborted fetuses limit widespread use of these donor sources. Given these limitations in supply of adult and fetal RPE grafts, the potential of alternative donor sources have been studied. Human pluripotent stem cells provide significant advantages as a source of RPE cells for transplantation. Their pluripotent developmental potential may enable their differentiation into authentic functional RPE cells, and given their potential for infinite self renewal, they may serve as an unlimited donor source of RPE cells. Indeed, it has been demonstrated that human embryonic stem cells (hESCs) and human induced pluripotent stem cells (iPS) may differentiate into RPE cells in vitro, attenuate retinal degeneration and preserve visual function after subretinal transplantation to the Royal College of Surgeons (RCS) rat model of retinal degeneration that is caused by RPE dysfunction. Therefore, pluripotent stem cells may be an unlimited source for the production of RPE cells.

Current protocols for the derivation of RPE cells from pluripotent stem cells yields mixed populations of pigmented and non-pigmented cells. However, pure populations of pigmented cells are desired for the usage of RPE cells in basic research, drug discovery and cell therapy. So far clusters of RPE cells have been identified as areas of dark pigmentation within cultures of multiple subtypes of differentiated cells and were mechanically dissected and isolated on the basis of their pigmentation. This approach is operator dependent, work intensive, depends on subjective judgment, inconsistent, inaccurate and cannot provide pure populations of pigmented cells.

Klimanskaya et al [Methods in Enzymology, Vol. 418, p.169-194, 2006] teaches that it is difficult to dissociate RPE cells following differentiation and accordingly sorting by FACS is not recommended.

Additional background art relevant to the present invention includes Rowland et al., J. Cell. Physiol. 227: 457-466, 2012 and Shi et al Stem cell Research and Therapeutics, Chapter I, pages 1-24.

SUMMARY OF THE INVENTION

According to an aspect of some embodiments of the present invention there is provided a method of selecting retinal pigmented epithelial (RPE) cells from a mixed population of cells, comprising:

(a) analyzing the cells of the mixed population of cells for at least one of the following parameters:

(i) cells which autofluorescence above a predetermined threshold;

(ii) cells which express CD81 above a predetermined threshold; and (iii) cells which scatter light perpendicular to a laser beam above a predetermined threshold; and (b) selecting cells which are positive for at least one of the parameters, thereby sorting RPE cells from a mixed population of cells.

According to some embodiments of the present invention the RPE cells are characterized by expression of at least one marker selected from the group consisting of bestrophin, CRALBP, MITF and RPE65.

According to some embodiments of the present invention the RPE cells are generated by ex-vivo differentiating pluripotent stem cells towards an RPE lineage.

According to some embodiments of the present invention the pluripotent stem cells comprise embryonic stem cells (ESCs).

According to some embodiments of the present invention the pluripotent stem cells comprise induced pluripotent stem (iPS) cells.

According to some embodiments of the present invention the ex vivo differentiating is effected by culturing the pluripotent stem cells in a medium comprising at least one member of the transforming growth factor β (TGF β) superfamily.

According to some embodiments of the present invention the medium further comprises nicotinamide (NA).

According to some embodiments of the present invention the culturing comprises a first culture stage in a first medium comprising nicotinamide (NA), the first medium being devoid of the at least one member of the TGFβ superfamily and a second culture stage in a second medium comprising NA and the at least one member of the TGFβ superfamily.

According to some embodiments of the present invention, the first culture stage is effected for at least two days.

According to some embodiments of the present invention the at least one member of the TGFβ superfamily is selected from the group consisting of TGFβ1, TGFβ3 and activin A.

According to some embodiments of the present invention the selecting cells is performed using a fluorescence activated cell sorter (FACS).

According to some embodiments of the present invention the selecting cells which autofluoresce is performed using a 780/60 nm filter of a FACS.

According to some embodiments of the present invention the selecting cells which express CD81 is effected using an antibody which binds to CD81.

According to some embodiments of the present invention the antibody comprises a detectable moiety.

According to some embodiments of the present invention the method further comprises dispersing the mixed population of cells prior to the selecting.

According to some embodiments of the present invention the dispersing is performed using trypsin.

According to some embodiments of the present invention the method further comprises culturing the RPE cells following the selecting in a medium comprising nicotinamide.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawings will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
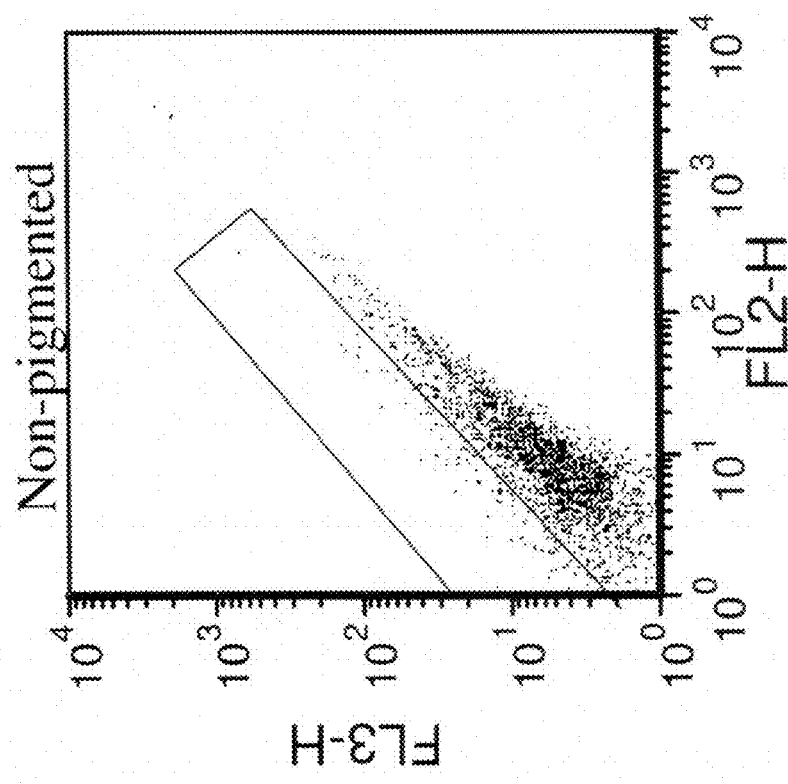
Figure 1B:
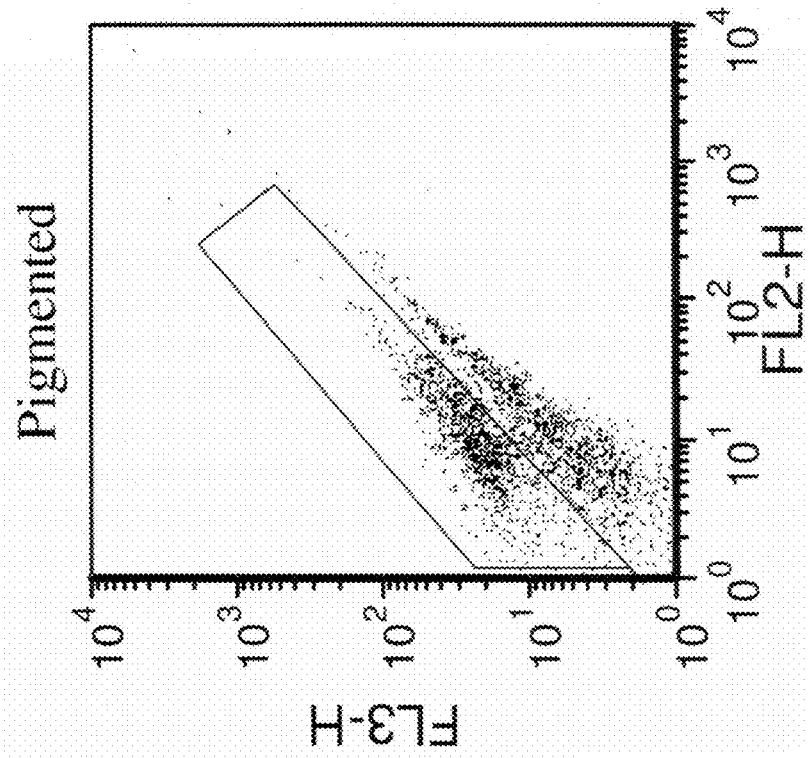

FIGS. 1A-1B: Single-cell suspensions were produced from mechanically-separated pigmented and non-pigmented clusters and analyzed by FACS as described in Materials and Methods. Dot plot analysis of unstained cells shows that the pigmented clusters are enriched with an autofluorescent cell-population, detected by the FL3 (780/60 nm) filter. This population was not detected in the non-pigmented clusters.

FIGS. 2A-2B: Single-cell suspensions were produced from mechanically-separated pigmented and non-pigmented clusters and analyzed by FACS, as described in Materials and Methods. Dot plot FSC/SSC analysis shows that the pigmented clusters are enriched with a high SSC value population, relative to the cells from the non-pigmented clusters.

Figure 3:
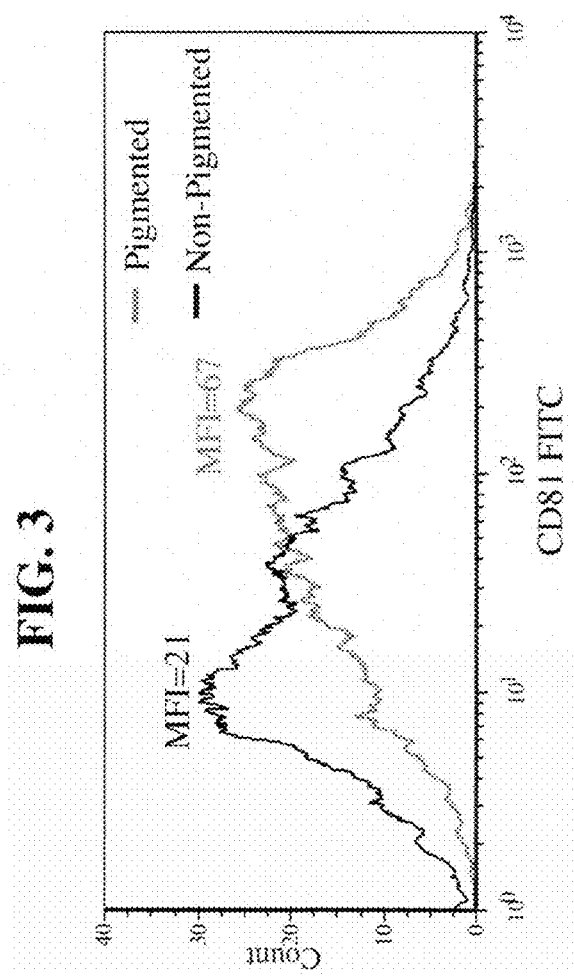

FIG. 3: Single-cell suspensions were produced from mechanically-separated pigmented and non-pigmented clusters and stained with FITC-labeled anti-CD81 antibody. FACS analysis of these cells shows that the pigmented clusters express high levels of CD81, relative to the non-pigmented clusters, as reflected by their mean fluorescence intensity (MFI).

Figure 4A:
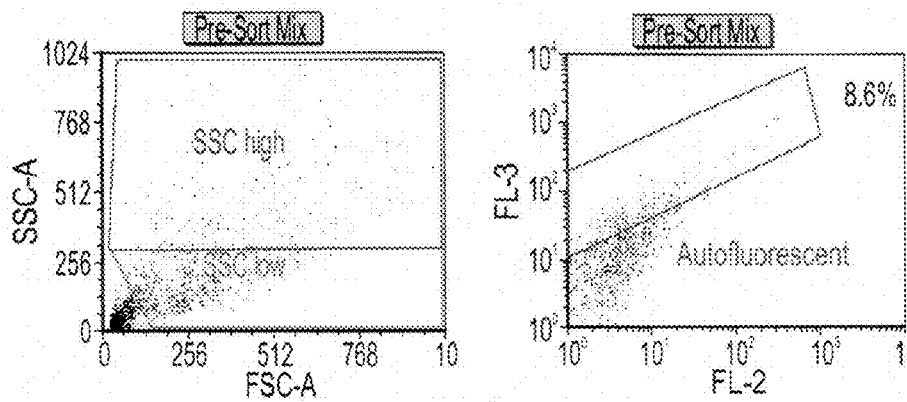
Figure 4B:
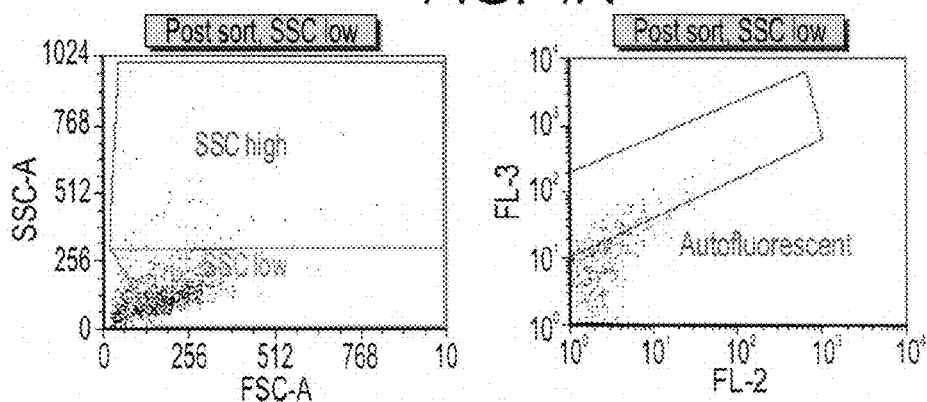
Figure 4C:
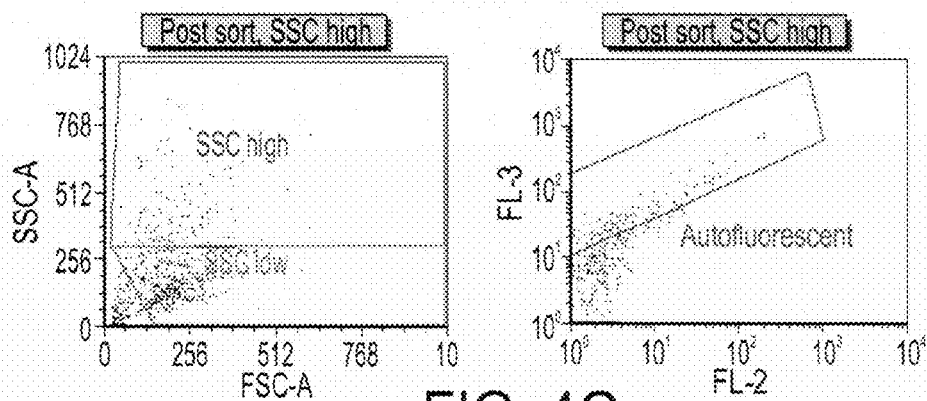
Figure 4D:
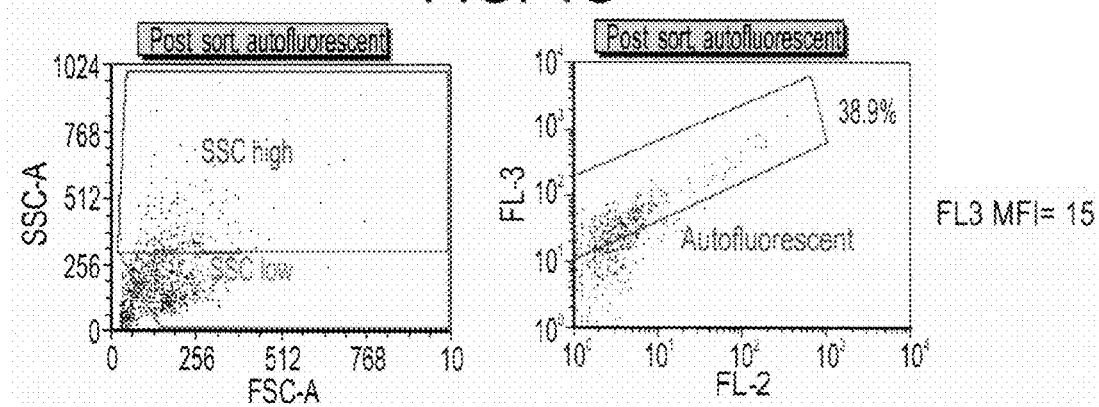

FIGS. 4A-4D: FACS sorting was carried out as described in Materials and Methods. Sorting gates were based on forward and side light scatter (FSC and SSC, respectively), as well as FL2 and FL3 parameters. This figure presents FACS analysis before ("pre-sort mix" dot plot, FIG. 4A) and after FACS sorting ("Post-sort SSC low", FIG. 4B: "Post-sort SSC high"; FIG. 4C and "Post-sort autofluorescent", FIG. 4D) dot plots. FSC/SSC dot plots are shown on the left column, demonstrating the location of "SSC high" and "SSC low" gates. The "Autofluorescent" gate is based on FL2 (576/26 nm) filter and the FL3 (780/60 nm) filter dot plots, which are shown on the right column.

FIGS. 5A-5C: Light microscopy of post-sorting cells of the "Autofluorescent", "SSC high" and "SSC low" populations, one day following the sorting and plating on 0.1% gelatine. Distinct cell morphologies can be identified at different sorted populations: dark-pigmented cytoplasm in the "Autofluorescent" sorted population, light and non-granulated cytoplasm in the "SSC low" sorted population and morphologies of both types in the "SSC high" sorted population.

FIGS. 6A-6C: Light microscopy of post-sorting cells of the "Autofluorescent", "SSC high" and "SSC low" populations eight days following the sorting and plating on gelatine. Distinct cell morphologies can be identified at the different sorted populations. The cells in the "Autofluorescent" sorted population acquire polygonal shape and dark cytoplasm, with high cell density, which implies relatively high proliferation rate. The "SSC low" sorted population have non-RPE morphology. The "SSC high" sorted population yields cells of both cell types.

FIGS. 7A-7C: Light microscopy of post-sorting cells of the "Autofluorescent", "SSC high" and "SSC low" populations, 16 days following the sorting and plating on gelatine. Significant differences were found in cell morphology of the "SSC low" population, in comparison with the "autofluorescent" and "SSC high" progeny. The cells in the "Autofluorescent" sorted population had polygonal shapes and dark cytoplasm, typical to mature RPE cells. The cells in the "SSC high" sorted population were similar to the "Autofluorescent" cells, suggesting that the RPE cells of took over the culture, because of their high proliferation rate. The cells in the "SSC low" were large, had light cytoplasm and almost did not proliferate. Some of these cells gained neuronal-like shapes.

FIGS. 8A-8B: Fluorescent microscopy of post-sorting cells of the "Autofluorescent" and the "SSC low" populations, two weeks after the sorting and plating on gelatine. Immunofluorescent staining was carried out as described in Materials and Methods, using antibodies specific to bestrophin (red) and CRALBP (green). The cells' nuclei were counterstained with DAPI (blue). The cells in the "Autofluorescent" sorted population were positively stained with these markers, in contrast with the negative cells in the "SSC low" population. Bestrophin was expressed by 88% of the cells (221 of 251 cells) and CRALBP was expressed by 75% of the cells (189 of 251 cells).

DESCRIPTION OF SPECIFIC EMBODIMENTS OF THE INVENTION

The present invention, in some embodiments thereof, relates to methods of selecting retinal pigmented epithelial cells (RPE cells).

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Current protocols for the derivation of retinal pigmented epithelium (RPE) cells from pluripotent stem cells yields mixed populations of pigmented and non-pigmented cells. However, pure populations of pigmented cells are desired for the usage of RPE cells in basic research, drug discovery and cell therapy. So far clusters of RPE cells have been identified as areas of dark pigmentation within cultures of multiple subtypes of differentiated cells and were mechanically dissected and isolated on the basis of their pigmentation. This approach is operator dependent, work intensive, depends on subjective judgment, inconsistent, inaccurate and cannot provide pure populations of pigmented cells.

To overcome these hurdles, the present inventors developed a method for the purification of RPE cells by fluorescence activated cell sorting (FACS). The present inventors employed FACS sorting to purify RPE cells from mixed-populations of differentiated cells, using novel criteria. The RPE cells were sorted on the basis of their physical properties of autofluorescence (FIGS. 1A-1B) and/or granularity (FIGS. 2A-2B), and/or on the basis of specific membrane markers, such as CD81 (FIG. 3). The cells after sorting had a mature RPE polygonal and pigmented phenotype (FIGS. 5-7) and expressed RPE specific markers (FIG. 8) as measured by immunohistochemistry.

Thus, according to one aspect of the present invention there is provided a method of selecting retinal pigmented epithelial (RPE) cells from a mixed population of cells, comprising:

(a) analyzing the cells of the mixed population of cells for at least one of the following parameters:

(i) cells which autofluorescence above a predetermined threshold;

(ii) cells which express CD81 above a predetermined threshold; and (iii) cells which scatter light perpendicular to a laser beam above a predetermined threshold; and (b) selecting cells which are positive for at least one of the parameters, thereby sorting RPE cells from a mixed population of cells.

As used herein, the phrase "retinal pigmented epithelial cells (RPE)" refers to cells of a cell type functionally similar to that of native RPE cells which form the pigmented cell layer of the retina (e.g. upon transplantation within an eye, they exhibit functional activities similar to those of native RPE cells).

RPE cells may be identified by expression of particular RPE marker proteins—e.g. bestrophin, cellular retinaldehyde-binding protein (CRALBP) retinal pigment epithelium specific protein (RPE65) 65 kDa, RPE transcription factors microphthalmia-associated transcription factor (MITF) and orthodenticle 2 isoform b homeobox protein (OTX2); tyrosinase, which functions in pigment synthesis; factors that are secreted by the RPE, such as pigment epithelium-derived factor (PEDF); membrane associated proteins bestrophin, extracellular matrix metalloproteinase inducer (EMMPRIN), and zona occludens 1 (ZO-1); proteins involved in phagocytosis, including the integrin aV subunit and Mer Tyrosine Kinase (MERTK).

According to a particular embodiment, the RPE cells that are selected express at least bestrophin and CRALBP.

According to one embodiment, the RPE cells are native RPE cells of the pigmented layer of the retina and have been removed from donors (e.g. cadavers, see for example Cruz et al., Progress in Retinal and Eye Research 26 (2007) 598-635; neonates or aborted fetuses, see for example Algvere et al., Graefes Arch Clin Exp Ophthalmol. 1994 December; 232(12):707-16). Alternatively, the RPE cells may be somatic cells from a different source (e.g. neuronal cells) which have undergone trans-differentiation, see for example Opas et al., Int. J. Dev. Biol. 45: 633-642 (2001)].

According to another embodiment, the RPE cells are differentiated ex vivo from immortalized cell lines.

According to still another embodiment, the RPE cells are differentiated ex vivo from stem cells (SC).

As used herein, the phrase "stem cells" refers to cells which are capable of remaining in an undifferentiated state (e.g., pluripotent or multipotent stem cells) for extended periods of time in culture until induced to differentiate into other cell types having a particular, specialized function (e.g., fully differentiated cells). Preferably, the phrase "stem cells" encompasses embryonic stem cells (ESCs), induced pluripotent stem cells (iPS), adult stem cells and hematopoietic stem cells. The stem cells are typically mammalian cells, such as for example human stem cells, rodent stem cells (e.g. mouse or rat) or primate stem cells (e.g. monkey).

The phrase "adult stem cells" (also called "tissue stem cells" or a stem cell from a somatic tissue) refers to any stem cell derived from a somatic tissue [of either a postnatal or prenatal animal (especially the human)]. The adult stem cell is generally thought to be a multipotent stem cell, capable of differentiation into multiple cell types. Adult stem cells can be derived from any adult, neonatal or fetal tissue such as adipose tissue, skin, kidney, liver, prostate, pancreas, intestine, and placenta.

The stem cells utilized by the present invention may also be bone marrow (BM)-derived stem cells including hematopoietic, stromal or mesenchymal stem cells (Dominici, M et al., 2001. Bone marrow mesenchymal cells: biological properties and clinical applications. J. Biol. Regul. Homeost. Agents. 15: 28-37). BM-derived stem cells may be obtained from iliac crest, femora, tibiae, spine, rib or other medullar spaces.

Mesenchymal stem cells give rise to one or more mesenchymal tissues (e.g., pancreatic, adipose, osseous, cartilaginous, elastic and fibrous connective tissues, myoblasts) as well as to tissues other than those originating in the embryonic mesoderm (e.g., neural cells) depending upon various influences from bioactive factors such as cytokines. Although such cells can be isolated from embryonic yolk sac, placenta, umbilical cord, fetal and adolescent skin, blood and other tissues, their abundance in the BM far exceeds their abundance in other tissues and as such isolation from BM is presently preferred.

Methods of isolating, purifying and expanding mesenchymal stem cells (MSCs) are known in the arts and include, for example, those disclosed by Caplan and Haynesworth in U.S. Pat. No. 5,486,359 and Jones E. A. et al., 2002, Isolation and characterization of bone marrow multipotential mesenchymal progenitor cells, Arthritis Rheum. 46(12): 3349-60.

Preferably, mesenchymal stem cell cultures are generated by diluting BM aspirates (usually 20 ml) with equal volumes of Hank's balanced salt solution (HBSS; GIBCO Laboratories, Grand Island, N.Y., USA) and layering the diluted cells over about 10 ml of a Ficoll column (Ficoll-Paque; Pharmacia, Piscataway, N.J., USA). Following 30 minutes of centrifugation at 2,500×g, the mononuclear cell layer is removed from the interface and suspended in HBSS. Cells are then centrifuged at 1,500×g for 15 minutes and resuspended in a complete medium (MEM, a medium without deoxyribonucleotides or ribonucleotides; GIBCO); 20% fetal calf serum (FCS) derived from a lot selected for rapid growth of MSCs (Atlanta Biologicals, Norcross, Ga.); 100 units/ml penicillin (GIBCO), 100 µg/ml streptomycin (GIBCO); and 2 mM L-glutamine (GIBCO). Resuspended cells are plated in about 25 ml of medium in a 10 cm culture dish (Corning Glass Works, Corning, N.Y.) and incubated at 37° C. with 5% humidified $CO_2$. Following 24 hours in culture, nonadherent cells are discarded, and the adherent cells are thoroughly washed twice with phosphate buffered saline (PBS). The medium is replaced with a fresh complete medium every 3 or 4 days for about 14 days. Adherent cells are then harvested with 0.25% trypsin and 1 mM EDTA (Trypsin/EDTA, GIBCO) for 5 min at 37° C., replated in a 6-cm plate and cultured for another 14 days. Cells are then trypsinized and counted using a cell counting device such as for example, a hemocytometer (Hausser Scientific, Horsham, Pa.). Cultured cells are recovered by centrifugation and resuspended with 5% DMSO and 30% FCS at a concentration of 1 to $2 \times 10^6$ cells per ml. Aliquots of about 1 ml each are slowly frozen and stored in liquid nitrogen.

To expand the mesenchymal stem cell fraction, frozen cells are thawed at 37° C., diluted with a complete medium and recovered by centrifugation to remove the DMSO. Cells are resuspended in a complete medium and plated at a concentration of about 5,000 cells/cm². Following 24 hours in culture, nonadherent cells are removed and the adherent cells are harvested using Trypsin/EDTA, dissociated by passage through a narrowed Pasteur pipette, and preferably replated at a density of about 1.5 to about 3.0 cells/cm². Under these conditions, MSC cultures can grow for about 50 population doublings and be expanded for about 2000 fold [Colter D C., et al. Rapid expansion of recycling stem cells in cultures of plastic-adherent cells from human bone marrow. Proc Natl Acad Sci USA. 97: 3213-3218, 2000].

According to one embodiment, the RPE cells are differentiated from pluripotent stem cells.

The phrase "pluripotent stem cells" as used herein, refers to cells which are capable of differentiating into the three embryonic germ cell layers, i.e., endoderm, ectoderm and mesoderm.

According to one embodiment, the pluripotent stem cells comprise embryonic stem cells and/or induced pluripotent stem cells.

The phrase "embryonic stem cells" refers to embryonic cells which are capable of differentiating into cells of all three embryonic germ layers (i.e., endoderm, ectoderm and mesoderm), or remaining in an undifferentiated state. The phrase "embryonic stem cells" may comprise cells which are obtained from the embryonic tissue formed after gestation (e.g., blastocyst) before implantation of the embryo (i.e., a pre-implantation blastocyst), extended blastocyst cells (EBCs) which are obtained from a post-implantation/pre-gastrulation stage blastocyst (see WO2006/040763) and embryonic germ (EG) cells which are obtained from the genital tissue of a fetus any time during gestation, preferably before 10 weeks of gestation.

Induced pluripotent stem cells (iPS; embryonic-like stem cells), are cells obtained by de-differentiation of adult somatic cells which are endowed with pluripotency (i.e., being capable of differentiating into the three embryonic germ cell layers, i.e., endoderm, ectoderm and mesoderm). According to some embodiments of the invention, such cells are obtained from a differentiated tissue (e.g., a somatic tissue such as skin) and undergo de-differentiation by genetic manipulation which re-programs the cell to acquire embryonic stem cells characteristics. According to some embodiments of the invention, the induced pluripotent stem cells are formed by inducing the expression of Oct-4, Sox2, Kfl4 and c-Myc in a somatic stem cell.

The embryonic stem cells of the present invention can be obtained using well-known cell-culture methods. For example, human embryonic stem cells can be isolated from human blastocysts. Human blastocysts are typically obtained from human in vivo preimplantation embryos or from in vitro fertilized (IVF) embryos. Alternatively, a single cell human embryo can be expanded to the blastocyst stage. For the isolation of human ES cells the zona pellucida is removed from the blastocyst and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 4-7 days. For further details on methods of preparation human ES cells see Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; and Gardner et al., [Fertil. Steril. 69: 84, 1998].

According to another embodiment, the ES cells are generated without the destruction of human embryos—see for example Chung et al Cell Stem cell, vol. 2, no. 2 7 Feb. 2008, pages 113-117.

It will be appreciated that commercially available stem cells can also be used with this aspect of the present invention. Human ES cells can be purchased from the NIH human embryonic stem cells registry (www(dot)escr(dot)nih(dot)gov). Non-limiting examples of commercially available embryonic stem cell lines are BG01, BG02, BG03, BG04, CY12, CY30, CY92, CY10, TE03 and TE32.

In addition, ES cells can be obtained from other species as well, including mouse (Mills and Bradley, 2001), golden hamster [Doetschman et al., 1988, Dev Biol. 127: 224-7], rat [Iannaccone et al., 1994, Dev Biol. 163: 288-92] rabbit [Giles et al. 1993, Mol Reprod Dev. 36: 130-8; Graves & Moreadith, 1993, Mol Reprod Dev. 1993, 36: 424-33], several domestic animal species [Notarianni et al., 1991, J Reprod Fertil Suppl. 43: 255-60; Wheeler 1994, Reprod Fertil Dev. 6: 563-8; Mitalipova et al., 2001, Cloning. 3: 59-67] and non-human primate species (Rhesus monkey and marmoset) [Thomson et al., 1995, Proc Natl Acad Sci USA. 92: 7844-8; Thomson et al., 1996, Biol Reprod. 55: 254-9].

Extended blastocyst cells (EBCs) can be obtained from a blastocyst of at least nine days post fertilization at a stage prior to gastrulation. Prior to culturing the blastocyst, the zona pellucida is digested [for example by Tyrode's acidic solution (Sigma Aldrich, St Louis, Mo., USA)] so as to expose the inner cell mass. The blastocysts are then cultured as whole embryos for at least nine and no more than fourteen days post fertilization (i.e., prior to the gastrulation event) in vitro using standard embryonic stem cell culturing methods.

EG cells are prepared from the primordial germ cells obtained from fetuses of about 8-11 weeks of gestation (in the case of a human fetus) using laboratory techniques known to anyone skilled in the arts. The genital ridges are dissociated and cut into small chunks which are thereafter disaggregated into cells by mechanical dissociation. The EG cells are then grown in tissue culture flasks with the appropriate medium. The cells are cultured with daily replacement of medium until a cell morphology consistent with EG cells is observed, typically after 7-30 days or 1-4 passages. For additional details on methods of preparation human EG cells see Shamblott et al., [Proc. Natl. Acad. Sci. USA 95: 13726, 1998] and U.S. Pat. No. 6,090,622.

Induced pluripotent stem cells (iPS) (embryonic-like stem cells) can be generated from somatic cells by genetic manipulation of somatic cells, e.g., by retroviral transduction of somatic cells such as fibroblasts, hepatocytes, gastric epithelial cells with transcription factors such as Oct-3/4, Sox2, c-Myc, and KLF4 [Yamanaka S, Cell Stem Cell. 2007, 1(1):39-49; Aoi T, et al., Generation of Pluripotent Stem Cells from Adult Mouse Liver and Stomach Cells. Science. 2008 Feb. 14. (Epub ahead of print); IH Park, Zhao R, West J A, et al. Reprogramming of human somatic cells to pluripotency with defined factors. Nature 2008; 451:141-146; K Takahashi, Tanabe K, Ohnuki M, et al. Induction of pluripotent stem cells from adult human fibroblasts by defined factors. Cell 2007; 131:861-872]. Other embryonic-like stem cells can be generated by nuclear transfer to oocytes, fusion with embryonic stem cells or nuclear transfer into zygotes if the recipient cells are arrested in mitosis.

It will be appreciated that undifferentiated stem cells are of a distinct morphology, which is clearly distinguishable from differentiated cells of embryo or adult origin by the skilled in the art. Typically, undifferentiated stem cells have high nuclear/cytoplasmic ratios, prominent nucleoli and compact colony formation with poorly discernible cell junctions. Additional features of undifferentiated stem cells are further described herein under.

Currently practiced ES culturing methods are mainly based on the use of feeder cell layers which secrete factors needed for stem cell proliferation, while at the same time, inhibit their differentiation. Feeder cell free systems have also been used in ES cell culturing, such systems utilize matrices supplemented with serum, cytokines and growth factors as a replacement for the feeder cell layer.

Feeder-Layer Based Cultures

Mouse feeder layers—The most common method for culturing ES cells is based on mouse embryonic fibroblasts (MEF) as a feeder cell layer supplemented with tissue culture medium containing serum or leukemia inhibitor factor (LIF) which supports the proliferation and the pluripotency of the ES cells [Thomson J A, Itskovitz-Eldor J, Shapiro S S, Waknitz M A, Swiergiel J J, Marshall V S, Jones J M. (1998). Embryonic stem cell lines derived from human blastocysts. Science 282: 1145-7; Reubinoff B E, Pera M F, Fong C, Trounson A, Bongso A. (2000). Embryonic stem cell lines from human blastocysts: somatic differentiation in vitro. Nat. Biotechnol. 18: 399-404]. MEF cells are derived from day 12-13 mouse embryos in medium supplemented with fetal bovine serum. Under these conditions mouse ES cells can be maintained in culture as pluripotent stem cells, preserving their phenotypical and functional characteristics. However, unlike mouse ES cells, the presence of exogenously added LIF does not prevent differentiation of human ES cells. Furthermore, the use of feeder cells substantially increases the cost of production, and makes scale-up of human ES cell culture impractical. Additionally, the feeder cells are metabolically inactivated to keep them from outgrowing the stem cells, hence it is necessary to have fresh feeder cells for each splitting of human ES culture. Since at present, the separation of feeder cell components from embryonic cells prepared in bulk culture cannot be efficiently achieved, feeder cell layer-prepared ES cultures are not suitable for human therapy.

ES cells can also be cultured on MEF under serum-free conditions using serum replacement supplemented with basic fibroblast growth factor (bFGF) [Amit M, Carpenter M K, Inokuma M S, Chiu C P, Harris C P, Waknitz M A, Itskovitz-Eldor J, Thomson J A. (2000). Clonally derived human embryonic stem cell lines maintain pluripotency and proliferative potential for prolonged periods of culture. Dev. Biol. 227: 271-8]. Under these conditions the cloning efficiency of ES cells is 4 times higher than under fetal bovine serum. In addition, following 6 months of culturing under serum replacement the ES cells still maintain their pluripotency as indicated by their ability to form teratomas which contain all three embryonic germ layers. Although this system uses a better-defined culture conditions, the presence of mouse cells in the culture exposes the human culture to pathogens which restricts their use in cell-based therapy.

Human embryonic fibroblasts or adult fallopian epithelial cells as feeder cell layers—Human ES cells can be grown and maintained using human embryonic fibroblasts, cord blood fibroblasts or adult fallopian epithelial cells. When grown on these human feeder cells the human ES cells exhibit normal karyotypes, present alkaline phosphatase activity, express Oct-4 and other embryonic cell surface markers including SSEA-3, SSEA-4, TRA-1-60, and GCTM-2, form teratomas in vivo, and retain all key morphological characteristics [Richards M, Fong C Y, Chan W K, Wong P C, Bongso A. (2002). Human feeders support prolonged undifferentiated growth of human inner cell masses and embryonic stem cells. Nat. Biotechnol. 20: 933-6].

Foreskin feeder layers—Human ES cells can be cultured on human foreskin feeder layer as disclosed in U.S. patent application Ser. No. 10/368,045. Foreskin derived feeder cell layers consist of a complete animal-free environment suitable for culturing human ES cells. In addition, foreskin cells can be maintained in culture for as long as 42 passages since their derivation, providing the ES cells with a relatively constant environment. Under these conditions the human ES cells were found to be functionally indistinct from cells grown with alternate protocols (e.g., MEF). Following differentiation, ES cells expressed genes associated with all three embryonal germ layers, in vitro, and formed teratomas in vivo, consisting of tissue arising from all three germ layers. In addition, unlike human fallopian epithelial cells or human embryonic fibroblasts, human ES cells cultured on foreskin feeder layers were maintained in culture in a pluripotent and undifferentiated state for at least 87 passages.

Feeder-Free Cultures

Stem cells can be grown on a solid surface such as an extracellular matrix (e.g., Matrigel® or laminin) in the presence of a culture medium.

Various methods are known in the art to differentiate embryonic stem cells ex vivo into RPE cells, as summarized in Rowland et al., [Journal Cell Physiology, 227:457-466, 2012], incorporated herein by reference.

Two main methods for differentiating hESCs to RPE cells have been developed. One approach is to allow hESCs to overgrow (normally cultured on feeder fibroblasts) and induce spontaneous differentiation through growth factor (i.e. basic fibroblast growth factor—bFGF) removal from the maintenance medium.

The hESCs differentiate, overgrow their clean colony borders, and become multilayered in this continuous adherent culture method. Timescales vary between studies and specific cell lines used, but approximately 1-8 weeks after growth factor removal, brown-pigmented spots appear. These spots develop and expand over time. Approximately 6-14 weeks after the cells are seeded, the cells may be sorted as further described herein below.

The second primary method for differentiating hESC to RPE is through embryoid body (EB), or neurosphere, formation. According to this method, hESC EBs or neurospheres are generated by passaging colonies to a low attachment surface (e.g., gelatin or agarose) and culturing the resultant EBs in suspension for a varying amount of time, from approximately 1 to 3 weeks or longer, e.g. up to 9 months. After culture in suspension, the aggregates may be seeded on an adherent substrate (e.g., laminin- or poly-D-lysine/fibronectin/laminin-coated plates) and further differentiated.

Examples of factors that may be used during the directed differentiation process include, but are not limited to WNT antagonists (e.g., Dickkopf-1 [Dkk-1]) in combination with NODAL antagonists (e.g., Lefty-A, also a TGF-β ligand). Alternatively, the floating culture differentiation media may be supplemented with nicotinamide (vitamin B3), which is thought to stimulate factors in the TGF-b superfamily, which may help pattern RPE during development (Idelson et al., 2010, incorporated herein by reference). Alternatively, the neural induction medium may be supplemented with N2 supplement and heparin, or B27, while the embryoid bodies are in suspension. Additional factors that may be used include activin A, TGF-β1, and SU5402.

According to a preferred embodiment, the differentiating is effected in a medium comprising at least one member of the transforming growth factor β (TGF β) superfamily.

The phrase "transforming growth factor-β (TGFβ) superfamily growth factor", as used herein, denotes any member of the TGFβ superfamily of growth factors, such as transforming growth factor-β proteins, including the TGFβ1, TGFβ2, and TGFβ3 subtypes, as well as homologous ligands including activin (e.g., activin A, activin B, and activin AB), nodal, anti-mullerian hormone (AMH), some bone morphogenetic proteins (BMP), e.g. BMP2, BMP3, BMP4, BMP5, BMP6, and BMP7, and growth and differentiation factors (GDF).

According to a preferred embodiment, the member of the TGFβ superfamily is preferably the TGFβ1, TGFβ3 growth factors or activin A or a combination of same.

The medium may comprise other components which promote RPE cell differentiation, such as for example nicotinamide.

Nicotinamide, NA, also known as "niacinamide", is the amide derivative form of Vitamin B3 (niacin) which is thought to preserve and improve beta cell function. NA has the chemical formula $C_6H_6N_2O$. NA is essential for growth and the conversion of foods to energy, and it has been used in arthritis treatment and diabetes treatment and prevention.

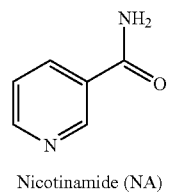

Nicotinamide (NA)

In the context of the present disclosure, the term NA also denotes derivatives of NA.

The term "derivative of nicotinamide (NA)" as used herein denotes a compound which is a chemically modified derivative of the natural NA. The chemical modification may include, for example, a substitution on the pyridine ring of the basic NA structure (via the carbon or nitrogen member of the ring), via the nitrogen or the oxygen atoms of the amide moiety, as well as deletion or replacement of a group, e.g. to form a thiobenzamide analog of NA, all of which being as appreciated by those versed in organic chemistry. The derivative in the context of the invention also includes the nucleoside derivative of NA (e.g. nicotinamide adenine). A variety of derivatives of NA are described, some also in connection with an inhibitory activity of the PDE4 enzyme (WO03/068233; WO02/060875; GB2327675A), or as VEGF-receptor tyrosine kinase inhibitors (WO01/55114). For example, the process of preparing 4-aryl-nicotinamide derivatives (WO05/014549).

According to an exemplary embodiment the culturing is effected in two stages—the first stage comprises culturing in a medium comprising NA (the medium being devoid of the TGFβ superfamily member) and the second stage comprises culturing in a medium comprising both the NA and the TGFβ superfamily member (e.g. activin).

The first and the second stage are typically effected for at least two days, more preferably for about two weeks.

Optionally, the first and second stage are effected in suspension i.e. as freely floating cells, wherein the majority of the cells freely float in the medium as single cells, as cell clusters and/or as cell aggregates. In other words, the cells survive and propagate in the medium without being attached to a substrate.

According to another embodiment at least one of the stages is performed as an adherent culture (i.e. flat culture) as taught by Vugler et al., [Exp Neurol. 2008 December; 214(2):347-61. Epub 2008 Sep. 27, incorporated herein by reference].

Following the second stage, the cells are typically cultured for at least 4 weeks, more preferably, at least 5 weeks, at least 6 weeks, at least 7 weeks in the same medium but devoid of the TGFβ superfamily member.

A more detailed method for generating RPE cells from pluripotent stem cells is described in the Examples section below.

Sorting is typically effected no earlier than 4 weeks from the start of the directed differentiation protocol, although typically sorting is effected later i.e. at least one month, at least 6 weeks, at least seven weeks, at least two months, at least three months, at least four months, at least five months from the start of the differentiation protocol.

Prior to sorting, the generated or isolated cell populations are typically dispersed using cell dispersing agents. Preferably single cell populations are obtained. Examples of agents that may be used to disperse the cells include, but are not limited to collagenase, dispase, accutase, trypsin (e.g.

trypsin-EDTA), papain. Alternatively, or additionally trituration may also be performed to increase the dispersal of the cells.

An exemplary concentration of trypsin that may be used is 0.005-0.1% (e.g. 0.01%) trypsin-EDTA the cells may be incubated with the dispersing agent for about 10-20 minutes, e.g. 15 minutes, at a temperature of about 37° C.

It will be appreciated that the mixed cell population from which the RPE cells are selected will comprise different cell types, depending on the source of the RPE cells. Thus, for example, if the RPE cells are obtained from ex vivo differentiated pluripotent stem cells, the mixed cell population may comprise less differentiated cell types or even non-differentiated cell types. If the RPE cells are obtained from a donor, the mixed cell population may comprise other retinal cell types.

As mentioned, the RPE cells are selected according to one of the following criteria:

(i) cells which autofluorescence above a predetermined threshold;

(ii) cells which express CD81; and (iii) cells which scatter light perpendicular to a laser beam above a predetermined threshold.

Selecting cells which express CD81 is typically effected using an agent which binds specifically to CD81. Typically, the cells express sufficient CD81 on their membrane such that they are capable of being detected using methods such as FACS, MACS and immunospanning as further described herein below.

Typically, the selecting is effected using antibodies that are capable of specifically recognizing this cell-surface protein, although the present invention contemplates additional agents such as polynucleotides or small molecules.

Antibodies which recognize CD81 may be obtained according to methods known in the art or may be obtained from commercial sources.

If the CD81 antibody is attached to a magnetic moiety (either directly, or indirectly through a cognate binding molecule), the heterogeneous cell population may be enriched for EpCAM$^+$ cells by magnetic activated cell separation.

If the CD81 antibody is attached is attached to an affinity moiety, the heterogeneous cell population may be enriched for CD81$^+$ cells by affinity purification with the cognate binding molecule. Thus, for example, if the CD81 antibody is attached to biotin, the heterogenous cell population may be depleted of CD81$^+$ cells by purification with strepavidin beads or column. The CD81$^+$ cells can subsequently be retrieved. If, for example the CD81 antibody is attached to an antibody or an Fc of an antibody, the heterogenous cell population may be depleted of CD81$^+$ cells by purification with protein A beads or column. The CD81$^+$ cells can subsequently be retrieved. If the CD81 antibody is attached is attached to a fluorescent moiety, the heterogeneous cell population may be enriched for CD81$^+$ cells by using a fluorescence-activated cell sorter (FACS).

A Flow Cytometer typically consists of a laser light source, flow measurement chamber, and an optical system consisting of lenses, filters, and light detectors. Two photomultiplier tubes (light detectors), one at 180 degrees and one at 90 degrees to the laser, are used to measure forward (FSC) and right-angle scatter (SSC), respectively. Three fluorescence detectors, each consisting of a filter and photomultiplier tube, are used to detect fluorescence. The three detectors sense green (FL1—530 nm), orange (FL2—585 nm), and red fluorescence (FL3—650 nm). Cells are identified by sort logic applied to all five of the detector signals (FSC, SSC, FL1, FL2, FL3) using a computer.

Exemplary Flow Cytometers that may be used in this aspect of the present invention are manufactured by companies such as Becton Dickinson (USA), Backman Coulter (USA), Partec (Germany).

The FACS machine may be set such that cells of a particular forward scatter and/or side scatter are selected. Forward-scattered light (FSC) is proportional to cell-surface area or size. FSC is a measurement of mostly diffracted light and is detected just off the axis of the incident laser beam in the forward direction by a photodiode. FSC provides a suitable method of detecting particles greater than a given size independent of their fluorescence.

Side-scattered light (SSC) is proportional to cell granularity or internal complexity. SSC is a measurement of mostly refracted and reflected light that occurs at any interface within the cell where there is a change in refractive index. SSC is collected at approximately 90 degrees to the laser beam by a collection lens and then redirected by a beam splitter to the appropriate detector.

The present invention contemplates selecting RPE cells using a FACS based on additional parameters.

For example, the present inventors have shown that by selecting cells from a mixed cell population which autofluoresce using FACS it is possible to select for RPE cells. According to this embodiment, autofluorescent cells may be sorted using a 780/60 nm filter (FL3-H). The FACS may be set at a voltage of about 429 volts when using this filter.

The present inventors have further shown that by selecting cells from a mixed cell population which have a high side scatter value using FACS it is possible to select for RPE cells. The FACS may be set at a voltage of about 305 volts when testing for this parameter.

It will be appreciated that the present invention contemplates selecting cells based on more than one of the above identified parameters—e.g. two of the above identified parameters or even all three of the above identified parameters.

Following sorting, the percent of RPE cells in the culture may be examined—for example by using immunohistochemistry techniques, as described in the Examples section herein below.

RPE cells may be expanded following sorting and optional verification. For expansion, they may be plated at low density on an extra cellular matrix, preferably poly-D-lysine and laminin, and cultured in serum-free KOM with NA. Under these culture conditions, the pigmented cells loose pigmentation and acquired a fibroid-like morphology. Following further prolonged culture and proliferation into high-density cultures, the cells re-acquired the characteristic polygonal shape morphology and pigmentation of RPE cells. The RPE cells may be expanded in suspension or in a monolayer. The expansion of the RPE cells in monolayer cultures may be modified to large scale expansion in bioreactors by methods well known to those versed in the art.

Harvesting of the cells may be performed by various methods known in the art. Non-limiting examples include mechanical dissection and dissociation with papain. Other methods known in the art are also applicable.

The sorted RPE cells may be transplanted to various target sites within a subject's eye. In accordance with one embodiment, the transplantation of the RPE cells is to the subretinal space of the eye, which is the normal anatomical location of the RPE (between the photoreceptor outer segments and the choroids). In addition, dependent upon migratory ability and/or positive paracrine effects of the cells, transplantation into additional ocular compartments can be considered including the vitreal space, the inner or outer retina, the retinal periphery and within the choroids.

Further, transplantation may be performed by various techniques known in the art. Methods for performing RPE transplants are described in, for example, U.S. Pat. Nos. 5,962,027, 6,045,791, and 5,941,250 and in Eye Graefes Arch Clin Exp Opthalmol March 1997; 235(3):149-58; Biochem Biophys Res Commun Feb. 24, 2000; 268(3): 842-6; Opthalmic Surg February 1991; 22(2): 102-8. Methods for performing corneal transplants are described in, for example, U.S. Pat. No. 5,755,785, and in Eye 1995; 9 (Pt 6 Su):6-12; Curr Opin Opthalmol August 1992; 3 (4): 473-81; Ophthalmic Surg Lasers April 1998; 29 (4): 305-8; Ophthalmology April 2000; 107 (4): 719-24; and Jpn J Ophthalmol November-December 1999; 43(6): 502-8. If mainly paracrine effects are to be utilized, cells may also be delivered and maintained in the eye encapsulated within a semi-permeable container, which will also decrease exposure of the cells to the host immune system (Neurotech USA CNTF delivery system; PNAS Mar. 7, 2006 vol. 103(10) 3896-3901).

In accordance with one embodiment, transplantation is performed via pars pana vitrectomy surgery followed by delivery of the cells through a small retinal opening into the sub-retinal space or by direct injection. Alternatively, cells may be delivered into the subretinal space via a trans-scleral, trans-choroidal approach. In addition, direct trans-scleral injection into the vitreal space or delivery to the anterior retinal periphery in proximity to the ciliary body can be performed.

The sorted RPE cells may be transplanted in various forms. For example, the RPE cells may be introduced into the target site in the form of cell suspension, or adhered onto a matrix, extracellular matrix or substrate such as a biodegradable polymer or a combination. The RPE cells may also be transplanted together (co-transplantation) with other retinal cells, such as with photoreceptors.

Thus, the invention also pertains to a composition comprising RPE cells generated as described herein and sorted by the method of the invention. The composition is preferably suitable for transplantation into the eye.

The compositions of the present invention may comprise between about 20,000-400,000 e.g. 100,000 cells.

Various eye conditions may be treated or prevented by the introduction of the RPE cells obtained by the method of the invention to a subject's eye. The eye conditions may include retinal diseases or disorders generally associated with retinal dysfunction, retinal injury, and/or loss of retinal pigment epithelium. A non-limiting list of conditions which may be treated in accordance with the invention comprises retinitis pigmentosa, leber's congenital amaurosis, hereditary or acquired macular degeneration, age related macular degeneration (AMD), Best disease, retinal detachment, gyrate atrophy, choroideremia, pattern dystrophy as well as other dystrophies of the RPE, Stargardt disease, RPE and retinal damage due to damage caused by any one of photic, laser, inflammatory, infectious, radiation, neovascular or traumatic injury.

As used herein, the term "treating" or "treatment" refers to the therapeutic as well as the prophylactic effect of the hSC-derived RPE cells of the invention on a subject's eye condition, the effect may generally include, amelioration of symptoms associated with the conditions, lessening of severity or curing the condition, more specifically, the effect may include reversal of damage caused to the treated subject's retina and RPE, improved function of the subject's retina, rebuilding of the subject's retina and RPE by replacement and/or support of failing host retinal and RPE cells, directly or by paracrine effect as well as to the prophylactic effect which may be exhibited by the attenuation, inhibition or cessation in damage caused to the subject's retina as a result of the condition.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

FACS-Sorting Separation of RPE Pigmented Cells from Non-Pigmented Cells

Materials and Methods hESC maintenance: hESCs were maintained on human foreskin fibroblasts treated for 2.5 hours with 10 µg/ml mitomycin-C (Sigma, St. Louis, Mo.), and plated in gelatin-coated 9.5 cm$^2$ well plates (Nunc, Glostrup, Denmark; 3×10$^5$ feeders/well). HES-1 cells were routinely cultured in 85% knockout DMEM medium supplemented with 14% knockout serum replacement, 1 mM L-glutamine, 1% nonessential amino acids (10 mM of each amino acid), 50 U/ml penicillin, 50 µg/ml streptomycin, (all from Gibco, Carlsbad, Calif.) and 4 ng/ml basic fibroblast growth factor (bFGF, Cytolab, Rehovot, Israel). The medium was changed every day. The cells were passaged weekly as small clusters following digestion with Collagenase type IV (1 mg/ml, Gibco) for 1 hour.

Differentiation of hESCs to RPE-enriched spheres: HES-1 cells were differentiated to spheres, composed of RPE cells and other cell types as described in Idelson et al., Cell Stem Cell, 2009. 5(4): p. 396-408, the contents of which are incorporated herein by reference. Briefly, hESC colonies were detached from the tissue culture plates using collagenase IV (1 mg/ml; Gibco), cultured as floating clusters in knockout medium, comprised of KO-DMEM, 14% KO serum replacement, 1% nonessential amino acids, 2 mM L-glutamine, 50 U/ml penicillin, 50 mg/ml streptomycin (all from Gibco), and 10 mM nicotinamide (Sigma) in 6-well culture dishes (Costar, Corning Inc., Corning, N.Y.), pre-treated with 0.1% low-melting-temperature agarose (FMC BioProducts, Rockland, Me.). During the differentiation procedure, the culture medium was replaced twice a week. After 2 weeks 140 ng/ml activin A (PeproTech Inc, Rocky Hill, N.J.), was added to the medium for 2 weeks. Then, activin A was omitted from the medium and pigmented areas appeared in the floating spheres. The pigmented areas were mature and ready for further analysis or sorting, 7-11 weeks after differentiation was initiated.

Preparation of single cell suspension from mixed spheres: Single cell suspensions were prepared from 7-11 week spheres using 0.01% trypsin-EDTA (Gibco) treatment for 15 minutes at 37° C. Trypsinization was blocked by adding equal volume of DMEM supplemented with 10% fetal calf serum (Gibco). The cells were then centrifuged at 1200 rpm for 3', re-suspended in FACS sorting buffer (DMEM without phenol red and with HEPES, supplemented with 10% fetal calf serum, 2 mM L-glutamine, 50 U/ml penicillin, 50 mg/ml streptomycin (all from Gibco), 20 mM glucose and 10 mM nicotinamide (both from Sigma). To obtain single-cell suspension, the cells were then filtered through 35 µm filters (Becton-Dickinson, Franklin Lakes, N.J.).

FACS analysis and sorting: FACS analysis was performed using FACSCalibur (Becton-Dickinson) according to standard procedures. FITC-labeled anti-CD81 antibody was purchased from Becton-Dickinson.

Sorting was performed using FACSAria (Becton-Dickinson) through a 100 µm nozzle, at flow rate 1-2, using "purity" mode. Table 1, herein below summarizes the voltage values that were used to achieve optimal definition of the desired populations:

TABLE 1

| Parameter | Voltage |
|---|---|
| FSC | 3 |
| SSC | 305 |
| FL2 (576/26 nm) filter | 659 |
| FL3 (780/60 nm) filter | 429 |

The mixed population was sorted using the following gates: "autofluorescent" "SSC high" and "SSC low" (shown in FIG. 5).

Analysis of FACS data was carried out using FCS Express (de-novo software) and Cellquest (Becton-Dickinson) softwares.

Post sorting RPE cell growth: After the sorting, $1-1.5\times10^5$ cells were centrifuged, re-suspended in DMEM supplemented with 10% fetal calf serum (Gibco) and 10 mM nicotinamide and plated on glass coverslips, that were pre-treated with poly-D-lysine (30-70 KDa, 10 μg/ml; Sigma) and 0.1% porcine-gelatine (Sigma). Cells were grown for 24-48 hours and then the medium was replaced with KO DMEM supplemented with 15% knockout serum replacement, 1% nonessential amino acids, 2 mM glutamine, 50 U/ml penicillin, 50 mg/ml streptomycin (all from Gibco), and 10 mM nicotinamide.

Immunofluorescent staining: After 1-2 weeks, the cells were either photographed using standard light microscopy, or fixed with 4% paraformaldehyde, and incubated with primary and secondary antibodies stained with fluorescent dyes. Nuclei were counterstained with 4,6-diamidino-2-phenylindole (DAPI; Vector Laboratories, Burlingame, Calif.). The antibodies used for these stainings were: rabbit anti CRALBP, (Santa Cruz, Calif.), followed by FITC-labeled swine anti-rabbit antibody (DAKO, Glostrup, Denmark) and mouse anti-bestrophin (Novus Biologicals, Littleton, Colo.), followed by Cy3-labelled goat anti mouse antibody (Jackson ImmunoResearch Laboratories, West Grove, Pa.).

Results

To develop protocols for purification of RPE by sorting, the present inventors initially identified novel markers and properties of RPE cells that would distinguish them from other differentiated cells. For this purpose, differentiation to cultures enriched with pigmented RPE cells within a mixture of non pigmented differentiated cells was carried out using a protocol described in materials and methods. A crude mechanical dissection was performed that separated the pigmented from the non-pigmented cell clusters. The two separated cell populations were disaggregated into single cell suspensions and compared by FACS analysis. The comparison enabled the identification of the following markers and properties that further allowed sorting of the pigmented cells:

1. The pigmented cells are auto-fluorescent, relatively to the non-pigmented cells.

FACS analysis of the pigmented and the non-pigmented clusters demonstrated auto-fluorescent population in the 780/60 nm filter (FL3-H), which was unique to the pigmented clusters, and did not exist within the non-pigmented clusters (FIG. 1).

2. The pigmented cells are enriched with a high side scatter population.

FACS analysis of visible light scatter in the direction of the FACS laser beam (forward scatter, FSC) and perpendicular to the laser beam (side light scatter, SSC), showed that the pigmented clusters are enriched with cells that have high SSC value, in contrast with the cells from the non-pigmented clusters that had relatively low SSC value (FIG. 2). These differences in the SSC levels, reflects the disparity in the granularity of the pigmented and the non-pigmented cells, since RPE cells contain melanin-granules in their cytoplasm. These cytoplasmic granules turn the laser beam aside, resulting in high SSC values.

3. The pigmented cells express high levels of CD81, relatively to the non-pigmented cells.

In order to identify extra-cellular markers that may be utilized to distinguish the pigmented from the non-pigmented cells, FACS analysis of these cells was performed using antibodies specific to candidate extra-cellular proteins. This analysis showed higher levels of CD81 in the pigmented population, relatively to the non-pigmented population, as revealed by their mean fluorescence intensity (FIG. 3).

Single cell suspensions were produced from mixed cell populations and sorted as described in materials and methods. While the pre-sorting population was composed of pigmented and non-pigmented cells, the post-sorting populations were enriched with pigmented cells. FIG. 4 demonstrates the differences between the pre-sort and the post-sort populations in one representative experiment. In this experiment, the autofluorescent-gated population was enriched from 8.6% in the pre-sort population to 38.9% at the autofluorescent post-sort population, about a 4.5-fold enrichment. Furthermore, the mean fluorescence intensity of the ungated cells in the FL3 (780/60 nm) filter was 2-fold higher in the autofluorescent post-sort population (MFI=15) than in the pre-sort population (MFI=7.5), suggesting that the autofluorescent population is highly enriched following FACS sorting.

After sorting, the cells were plated and grown on 0.1% gelatin-coated tissue culture plates. After one day, the cells attached to the plates and distinct cell morphologies appeared in the three sorted cell types, illustrated in FIG. 5. In the autofluorescent population, the cells had dark pigmented cytoplasm. In contrast, in the low SSC population, the cells had irregular shapes, a lighter cytoplasm, and no melanin granules. The high SSC population included cells of both types (FIG. 5).

One week later, a typical polygonal RPE morphology was observed in the autofluorescent sorted cells. The cells had dark cytoplasm, resulting from pigmented granules (FIG. 6). In contrast, the low SSC cells had variable cell morphologies, without cytoplasmic pigmented granules (FIG. 6). The progeny of the autofluorescent sorted cells were numerous, relatively to the low SSC sorted cells, indicating a higher proliferation rate of the autofluorescent cells (FIG. 6). The high SSC sorted cells were composed of a mixture of cells, representing both cell types (FIG. 6).

After 2 weeks in culture, the autofluorescent sorted cells had a mature RPE polygonal and pigmented phenotype, in contrast with the progeny of the low SSC sorted cells that almost did not proliferate and had a different morphology, of larger and irregular cells with light cytoplasm. Occasional neurite formation was detected within these cells (FIG. 7). The progeny of the high SSC sorted cells had morphology, similar to the autofluorescent sorted cells, presumably due to rapid proliferation of RPE cells in comparison with the non-RPE cells that were in the original high SSC sorted population.

After 2 weeks in culture, the progeny of the sorted populations were fixed and stained with antibodies directed to specific markers of RPE cells, as described in materials and methods. The autofluorescent sorted cells expressed the RPE related markers bestrophin and CRALBP, while the non-autofluorescent cells did not express these markers (FIG. 8). This finding supports the RPE identity of the sorted autofluorescent population.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of selecting mammalian retinal pigmented epithelial (RPE) cells suitable for cell therapy from a mixed population of cells which comprise non-pigmented cells, comprising:
   (a) ex vivo differentiating mammalian pluripotent stem cells towards an RPE lineage to generate a mixed population of cells which comprise pigmented and non-pigmented cells, said pigmented cells expressing at least one marker selected from the group consisting of bestrophin, CRALBP, MITF and RPE65; and
   (b) using a fluorescence activated cell sorter (FACS) with a 780/60 nm FACS filter to identify and select cells from said mixed population of cells which have high side light scatter relative to non-pigmented cells, wherein the FACS is set at about 305 volts or 429 volts and
   wherein the selected cells are pigmented and have said high side light scatter relative to the non-pigmented cells, thereby selecting mammalian RPE cells suitable for cell therapy.

2. The method of claim 1, further comprising culturing the cells from step (b) in a medium comprising nicotinamide.

3. The method of claim 1, wherein said pluripotent stem cells comprise embryonic stem cells (ESCs).

4. The method of claim 1, wherein said pluripotent stem cells comprise induced pluripotent stem (iPS) cells.

5. The method of claim 1, wherein said ex vivo differentiating is effected by culturing said pluripotent stem cells in a medium comprising activin A.

6. The method of claim 5, wherein said medium further comprises nicotinamide (NA).

7. The method of claim 6, wherein said nicotinamide is at a concentration of about 10 mM.

8. The method of claim 6, wherein said ex vivo differentiating of step (a) comprises at least two culturing steps: a first culturing step comprises culturing said pluripotent stem cells in a medium comprising nicotinamide, and a second culturing step comprises culturing said pluripotent stem cells in a medium comprising NA and activin A.

9. The method of claim 8, wherein said first culturing step is effected for at least two days.

10. The method of claim 1, wherein said ex vivo differentiating is effected by culturing said pluripotent stem cells in a medium comprising at least one member of a TGFβ superfamily which is selected from the group consisting of TGFβ1, TGFβ3 and activin A.

11. The method of claim 1, further comprising selecting cells that express CD81 from said mixed population of cells.

12. The method of claim 11, wherein said selecting cells which express CD81 is effected using an antibody which binds to CD81.

13. The method of claim 12, wherein said antibody comprises a detectable moiety.

14. The method of claim 1, further comprising dispersing said mixed population of cells prior to selecting the cells in step (b) and following said ex vivo differentiating in step (a).

15. The method of claim 14, wherein said dispersing is performed using trypsin.

16. A method of selecting mammalian retinal pigmented epithelial (RPE) cells suitable for cell therapy from a mixed population of cells which comprise non-pigmented cells, comprising:
   (a) ex vivo differentiating mammalian pluripotent stem cells towards an RPE lineage to generate a mixed population of cells which comprise pigmented and non-pigmented cells, said pigmented cells expressing at least one marker selected from the group consisting of bestrophin, CRALBP, MITF and RPE65; and
   using a fluorescence activated cell sorter (FACS) with a 780/60 nm FACS filter to identify and select cells from said mixed population of cells, wherein the FACS is set at about 305 volts or 429 volts and
   wherein the selected cells are pigmented, thereby selecting mammalian RPE cells suitable for cell therapy.

17. The method of claim 16, further comprising culturing the cells from step (b) in a medium comprising nicotinamide.

18. The method of claim 16, wherein said pluripotent stem cells comprise embryonic stem cells (ESCs).

19. The method of claim 16, wherein said pluripotent stem cells comprise induced pluripotent stem (iPS) cells.

20. The method of claim 16, wherein said ex vivo differentiating is effected by culturing said pluripotent stem cells in a medium comprising activin A.

21. The method of claim 20, wherein said medium further comprises nicotinamide (NA).

22. The method of claim 21, wherein said nicotinamide is at a concentration of about 10 mM.

23. The method of claim 21, wherein said ex vivo differentiating of step (a) comprises at least two culturing steps: a first culturing step comprises culturing said pluripotent stem cells in a medium comprising nicotinamide, and a second culturing step comprises culturing said pluripotent stem cells in a medium comprising NA and activin A.

24. The method of claim 23, wherein said first culturing step is effected for at least two days.

25. The method of claim 16, wherein said ex vivo differentiating is effected by culturing said pluripotent stem cells in a medium comprising at least one member of a TGFβ superfamily which is selected from the group consisting of TGFβ1, TGFβ3 and activin A.

26. The method of claim 16, further comprising selecting cells that express CD81 from said mixed population of cells.

27. The method of claim 26, wherein said selecting cells which express CD81 is effected using an antibody which binds to CD81.

28. The method of claim 27, wherein said antibody comprises a detectable moiety.

29. The method of claim 16, further comprising dispersing said mixed population of cells prior to selecting the cells in step (b) and following said ex vivo differentiating in step (a).

30. The method of claim 29, wherein said dispersing is performed using trypsin.

* * * * *